US009526557B2

(12) United States Patent
Brannan

(10) Patent No.: US 9,526,557 B2
(45) Date of Patent: *Dec. 27, 2016

(54) ABLATION DEVICES UTILIZING EXOTHERMIC CHEMICAL REACTIONS, SYSTEM INCLUDING SAME, AND METHODS OF ABLATING TISSUE USING SAME

(71) Applicant: COVIDIEN LP, Mansfield, MA (US)

(72) Inventor: Joseph D. Brannan, Erie, CO (US)

(73) Assignee: COVIDIEN LP, Mansfield, MA (US)

( * ) Notice: Subject to any disclaimer, the term of this patent is extended or adjusted under 35 U.S.C. 154(b) by 337 days.

This patent is subject to a terminal disclaimer.

(21) Appl. No.: 14/242,019

(22) Filed: Apr. 1, 2014

(65) Prior Publication Data
US 2014/0214017 A1    Jul. 31, 2014

Related U.S. Application Data

(63) Continuation of application No. 12/861,333, filed on Aug. 23, 2010, now Pat. No. 8,690,866.

(51) Int. Cl.
| A61B 18/14 | (2006.01) |
| A61B 18/06 | (2006.01) |
| A61B 18/00 | (2006.01) |
| A61B 18/04 | (2006.01) |

(52) U.S. Cl.
CPC ...... *A61B 18/06* (2013.01); *A61B 2018/00023* (2013.01); *A61B 2018/00577* (2013.01); *A61B 2018/046* (2013.01); *A61B 2018/068* (2013.01)

(58) Field of Classification Search
CPC .............. A61B 18/06; A61B 2018/00023; A61B 2018/00577; A61B 2018/068; A61B 2018/046
See application file for complete search history.

(56) References Cited

U.S. PATENT DOCUMENTS

| 4,799,479 A | 1/1989 | Spears |
| 4,834,802 A | 5/1989 | Prier |
| 5,843,021 A | 12/1998 | Edwards et al. |

(Continued)

FOREIGN PATENT DOCUMENTS

| EP | 1977709 A1 | 10/2008 |
| WO | 0206421 | 1/2002 |

OTHER PUBLICATIONS

Cressman, Eric N.K., "Image-guided Thermochemical Ablation: Theoretical and Practical Considerations" 31.sup.st Annual InternationalConference of the IEEE EMBS, 2009 pp. 4291-4294.

*Primary Examiner* — Michael Peffley

(57) ABSTRACT

An ablation device includes a handle assembly including a distal end and a probe extending distally from the distal end of the handle assembly. The probe includes a heat-transfer portion and at least one fluid-flow path in fluid communication with the heat-transfer portion. The handle assembly includes at least one fluid reservoir in fluid communication with the at least one fluid-flow path and at least one apparatus configured to cause fluid flow between the at least one fluid reservoir and the heat-transfer portion. The probe is configured to apply thermal energy released by an exothermic chemical reaction that occurs when fluid from the at least one fluid reservoir is caused to flow to the heat-transfer portion.

18 Claims, 8 Drawing Sheets

(56) References Cited

U.S. PATENT DOCUMENTS

| | | | |
|---|---|---|---|
| 6,033,401 A * | 3/2000 | Edwards | A61B 17/00491 |
| | | | 606/214 |
| 6,416,491 B1 | 7/2002 | Edwards et al. | |
| 6,824,555 B1 | 11/2004 | Towler et al. | |
| 6,902,564 B2 | 6/2005 | Morgan et al. | |
| 7,252,665 B2 | 8/2007 | Starkebaum et al. | |
| 7,282,050 B2 | 10/2007 | Starkebaum et al. | |
| 8,690,866 B2 | 4/2014 | Brannan | |
| 2003/0131948 A1 | 7/2003 | Davidson et al. | |
| 2007/0100405 A1 | 5/2007 | Thompson et al. | |
| 2007/0219546 A1 | 9/2007 | Mody et al. | |
| 2007/0270789 A1 | 11/2007 | Berger | |
| 2008/0249521 A1 | 10/2008 | Dunning et al. | |
| 2010/0145304 A1 * | 6/2010 | Cressman | A61B 18/06 |
| | | | 604/506 |
| 2011/0106054 A1 * | 5/2011 | Osborne | A61B 17/8816 |
| | | | 604/518 |
| 2011/0295246 A1 * | 12/2011 | Prakash | A61B 18/1815 |
| | | | 606/33 |
| 2012/0215212 A1 * | 8/2012 | Selzer | A61B 18/04 |
| | | | 606/27 |

\* cited by examiner

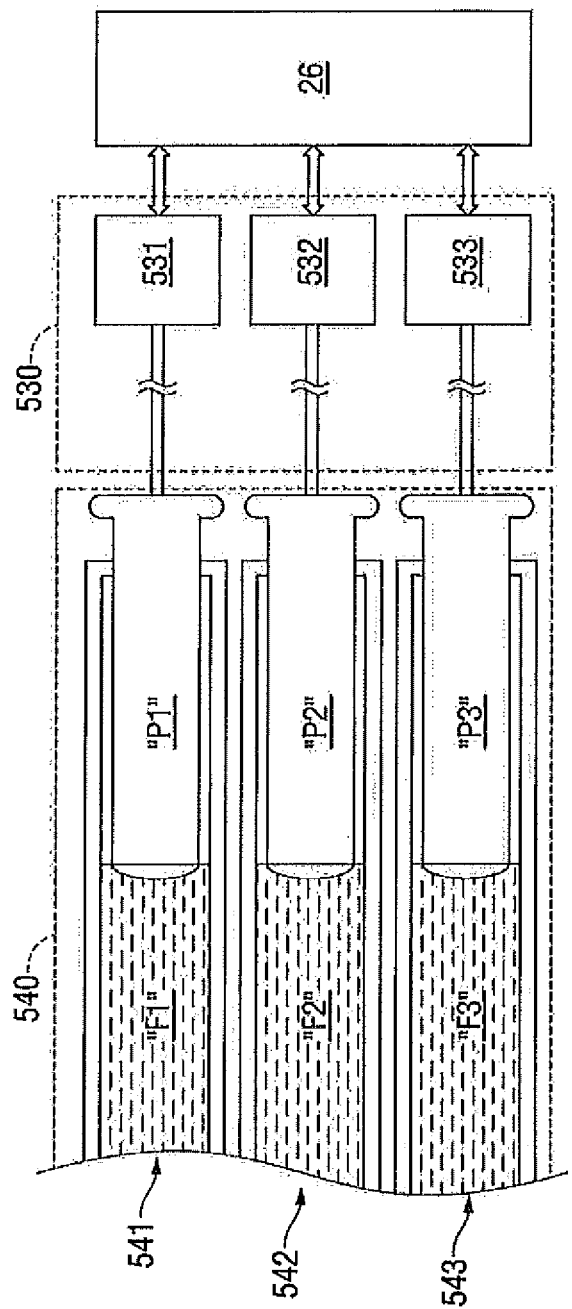

ABLATION DEVICES UTILIZING EXOTHERMIC CHEMICAL REACTIONS, SYSTEM INCLUDING SAME, AND METHODS OF ABLATING TISSUE USING SAME

CROSS-REFERENCE TO RELATED APPLICATIONS

The present application is a continuation of, and claims priority to, U.S. patent application Ser. No. 12/861,333, now U.S. Pat. No. 8,690,866, filed on Aug. 23, 2010, the entire contents of which is incorporated herein by reference.

BACKGROUND

1. Technical Field

The present disclosure relates to ablation devices suitable for use in tissue ablation applications and, more particularly, to ablation devices capable of utilizing exothermic chemical reactions, a system including the same, and methods of ablating tissue using the same.

2. Discussion of Related Art

Treatment of certain diseases requires the destruction of malignant tissue growths, e.g., tumors. Tumor treatment depends on a variety of factors such as the tumor's type, size, location, and the overall health of the patient. Treatment options may include hyperthermia therapy to heat and destroy tumor cells, cryoablation to freeze the tumor to kill the cells, thermochemical ablation therapy to thermally ablate the tumor by using direct injection of ethanol or acetic acid using ultrasound or other guidance and, in some cases, external beam radiation therapy may be used to destroy tumor cells.

In the treatment of diseases such as cancer, certain types of tumor cells have been found to denature at elevated temperatures that are slightly lower than temperatures normally injurious to healthy cells. Known treatment methods, such as hyperthermia therapy, heat diseased cells to temperatures above 41° C. while maintaining adjacent healthy cells below the temperature at which irreversible cell destruction occurs. These methods may involve applying electromagnetic radiation to heat, ablate and/or coagulate tissue. Treatment may involve inserting ablation probes into tissues where cancerous tumors have been identified. Once the probes are positioned, electromagnetic energy is passed through the probes into surrounding tissue.

Electrosurgical devices utilizing electromagnetic radiation have been developed for a variety of uses and applications. A number of devices are available that can be used to provide high bursts of energy for short periods of time to achieve cutting and coagulative effects on various tissues. There are a number of different types of apparatus that can be used to perform ablation procedures. Typically, microwave apparatus for use in ablation procedures include a microwave generator that functions as an energy source, and a microwave surgical instrument (e.g., microwave ablation probe) having an antenna assembly for directing the energy to the target tissue. The microwave generator and surgical instrument are typically operatively coupled by a cable assembly having a plurality of conductors for transmitting microwave energy from the generator to the instrument, and for communicating control, feedback and identification signals between the instrument and the generator.

During certain procedures, it can be difficult to assess the extent to which the microwave energy will radiate into the surrounding tissue, making it difficult to determine the area or volume of surrounding tissue that will be ablated. Tissue ablation devices capable of directing thermal energy to tissue without the use of microwave radiation may enable more precise ablation treatments, which may lead to shorter patient recovery times, fewer complications from undesired tissue damage, and improved patient outcomes.

Tissue ablation devices capable of directing thermal energy to heat, ablate and/or coagulate tissue without the use of electromagnetic radiation may enhance device portability and location independence, and may help to facilitate improved patient accessibility to hyperthermic treatments.

SUMMARY

The present disclosure relates to an ablation device including a handle assembly including a distal end and a probe extending distally from the distal end of the handle assembly. The probe includes a heat-transfer portion and at least one fluid-flow path in fluid communication with the heat-transfer portion. The handle assembly includes at least one fluid reservoir in fluid communication with the at least one fluid-flow path and at least one apparatus configured to cause fluid flow between the at least one fluid reservoir and the heat-transfer portion. The probe is configured to apply thermal energy released by an exothermic chemical reaction that occurs when fluid from the at least one fluid reservoir is caused to flow to the heat-transfer portion.

The present disclosure also relates to a system for ablating tissue including an ablation device capable of utilizing an exothermic chemical reaction. The ablation device includes a handle assembly including a cartridge unit and a probe extending distally from a distal end of the handle assembly. The cartridge unit includes a first chamber containing a first fluid and a second chamber containing a second fluid. The probe includes a mixing junction and first and second fluid-flow paths in fluid communication with the mixing junction. The first fluid-flow path is in fluid communication with the first chamber, and the second fluid-flow path is in fluid communication with the second chamber.

The present disclosure also relates to a method of delivering thermal energy to tissue including the initial step of providing an ablation device including a handle assembly and a probe operably coupled to the handle assembly. The probe includes a heat-transfer portion and at least one fluid-flow path defined therein and disposed in fluid communication with the heat-transfer portion. The handle assembly includes at least one fluid reservoir in fluid communication with the at least one fluid-flow path. The method also includes the steps of positioning the probe in tissue, causing an exothermic chemical reaction within the at least one fluid flow path of the probe, and delivering thermal energy released by the exothermic chemical reaction through the heat-transfer portion of the probe to tissue.

The present disclosure also relates to a method of delivering thermal energy to tissue including the initial step of providing an ablation device including a handle assembly and a probe extending distally from a distal end of the handle assembly. The handle assembly includes a cartridge housing a first chamber defined therein and configured to contain an acid and a second chamber defined therein and configured to contain a base. The probe includes a mixing junction and first and second fluid-flow paths in fluid communication with the mixing junction. The first fluid-flow path is in fluid communication with the first chamber, and the second fluid-flow path is in fluid communication with the second chamber. The method also includes the steps of positioning the probe in tissue, moving one or more moveable members operably coupled to the cartridge to cause fluid flow of the acid and the base to the mixing junction to cause an exothermic chemical reaction, and delivering thermal energy released by the exothermic chemical reaction through at least a portion of the probe to tissue.

BRIEF DESCRIPTION OF THE DRAWINGS

Objects and features of the presently disclosed ablation devices utilizing exothermic chemical reactions, system including the same, and methods of ablating tissue using the same will become apparent to those of ordinary skill in the art when descriptions of various embodiments thereof are read with reference to the accompanying drawings, of which:

FIG. 8 is a partial, schematic diagram of an apparatus capable of generating fluid flow by controlling the position of one or more pistons within one or more fluid reservoirs of a cartridge unit according to an embodiment of the present disclosure;

DETAILED DESCRIPTION

Figure 1:
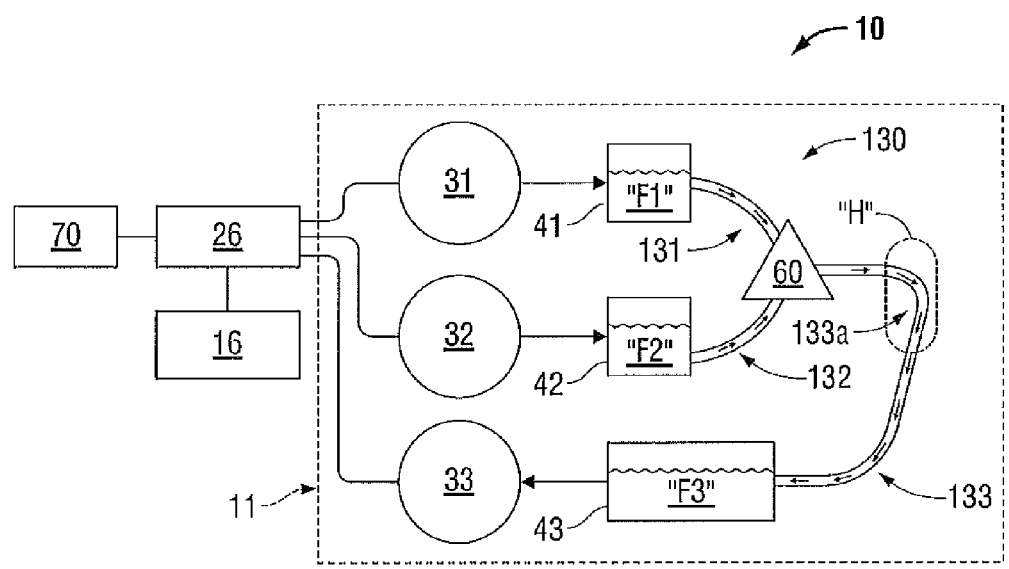
FIG. 1 is a block diagram of a heat-generating system for carrying out an exothermic chemical reaction to produce thermal energy according to an embodiment of the present disclosure.

Hereinafter, embodiments of the presently disclosed ablation devices utilizing exothermic chemical reactions, system including the same, and methods of ablating tissue using the same are described with reference to the accompanying drawings. Like reference numerals may refer to similar or identical elements throughout the description of the figures. As shown in the drawings and as used in this description, and as is traditional when referring to relative positioning on an object, the term "proximal" refers to that portion of the apparatus, or component thereof, that is closer to the user and the term "distal" refers to that portion of apparatus, or component thereof, that is farther from the user.

This description may use the phrases "in an embodiment," "in embodiments," "in some embodiments," or "in other embodiments," which may each refer to one or more of the same or different embodiments in accordance with the present disclosure. For the purposes of this description, a phrase in the form "A/B" means A or B. For the purposes of the description, a phrase in the form "A and/or B" means "(A), (B), or (A and B)". For the purposes of this description, a phrase in the form "at least one of A, B, or C" means "(A), (B), (C), (A and B), (A and C), (B and C), or (A, B and C)".

As it is used in this description, "fluid" generally refers to a liquid, a gas or both. As it is used in this description, "pressure" generally refers to positive pressure, negative pressure or both. As it is used in this description, "exothermic chemical reaction", or "exothermic reaction" for short, generally refers to a chemical reaction that releases energy in the form of heat.

As it is used in this description, "acid" generally refers to any chemical compound that, when dissolved in water, gives a solution with a hydrogen ion activity greater than in pure water, e.g., a pH less than 7.0 (at 25° C.) in its standard state. The strength of an acid or a base is determined by its ability to ionize in water. The percent ionization of an acid or base may be defined as the percent of the total molecules of the acid or base that react with water to form hydronium or hydroxyl ions. Acids that ionize 95% or better in water are usually referred to as strong acids. An acid that ionizes less than 95% in water may be referred to as a weak acid. There is no clear demarcation line between strong and weak acids and between strong and weak bases. Rather there is a continuum in the strengths of each.

As it is used in this description, "actuator" generally refers to any device that converts one form of applied power to a useable form of power that provides motion of a moveable member. Actuators may be generally classified into hydraulic, pneumatic, and electro-mechanical actuators. Electro-mechanical actuators generally include an electric motor and one or more drive train components to transfer and/or convert power provided by the electric motor to a moveable member. As it is used in this description, "switch" or "switches" includes any electrical actuators, mechanical actuators, electro-mechanical actuators (rotatable actuators, pivotable actuators, toggle-like actuators, buttons, etc.) or optical actuators.

As it is used in this description, "transmission line" generally refers to any transmission medium that can be used for the propagation of signals from one point to another. As it is used in this description, "length" may refer to electrical length or physical length. In general, electrical length is an expression of the length of a transmission medium in terms of the wavelength of a signal propagating within the medium. Electrical length is normally expressed in terms of wavelength, radians or degrees. For example, electrical length may be expressed as a multiple or sub-multiple of the wavelength of an electromagnetic wave or electrical signal propagating within a transmission medium. The wavelength may be expressed in radians or in artificial units of angular measure, such as degrees. The electric length of a transmission medium may be expressed as its physical length multiplied by the ratio of (a) the propagation time of an electrical or electromagnetic signal through the medium to (b) the propagation time of an electromagnetic wave in free space over a distance equal to the physical length of the medium. The electrical length is in general different from the physical length. By the addition of an appropriate reactive element (capacitive or inductive), the electrical length may be made significantly shorter or longer than the physical length.

Various embodiments of the present disclosure provide ablation devices capable of utilizing an exothermic chemical reaction to produce heat for treating tissue and methods of delivering ablative thermal energy to tissue.

Various embodiments of the presently disclosed ablation devices capable of utilizing an exothermic reaction and electrosurgical systems including the same are suitable for ablation and for use to pre-coagulate tissue for ablation-assisted surgical resection. Although various methods described hereinbelow are targeted toward ablation and the complete destruction of target tissue, it is to be understood that methods for directing thermal energy may be used with other therapies in which the target tissue is partially destroyed or damaged, such as, for example, to prevent the conduction of electrical impulses within heart tissue.

Figure 2:
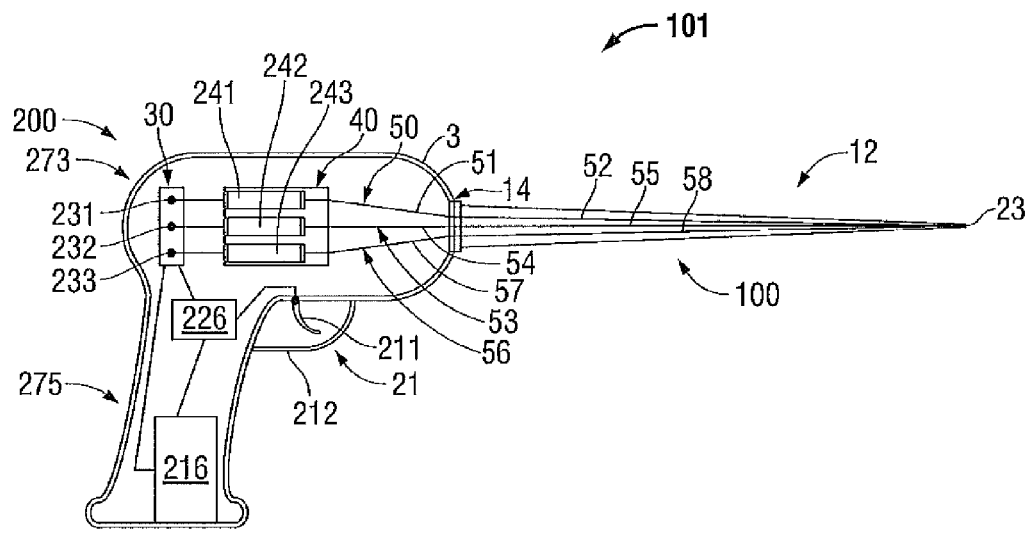
FIG. 2 is a schematic diagram of an embodiment of an ablation device capable of utilizing an exothermic chemical reaction for applying ablative thermal energy to tissue in accordance with the present disclosure.
Figure 3:
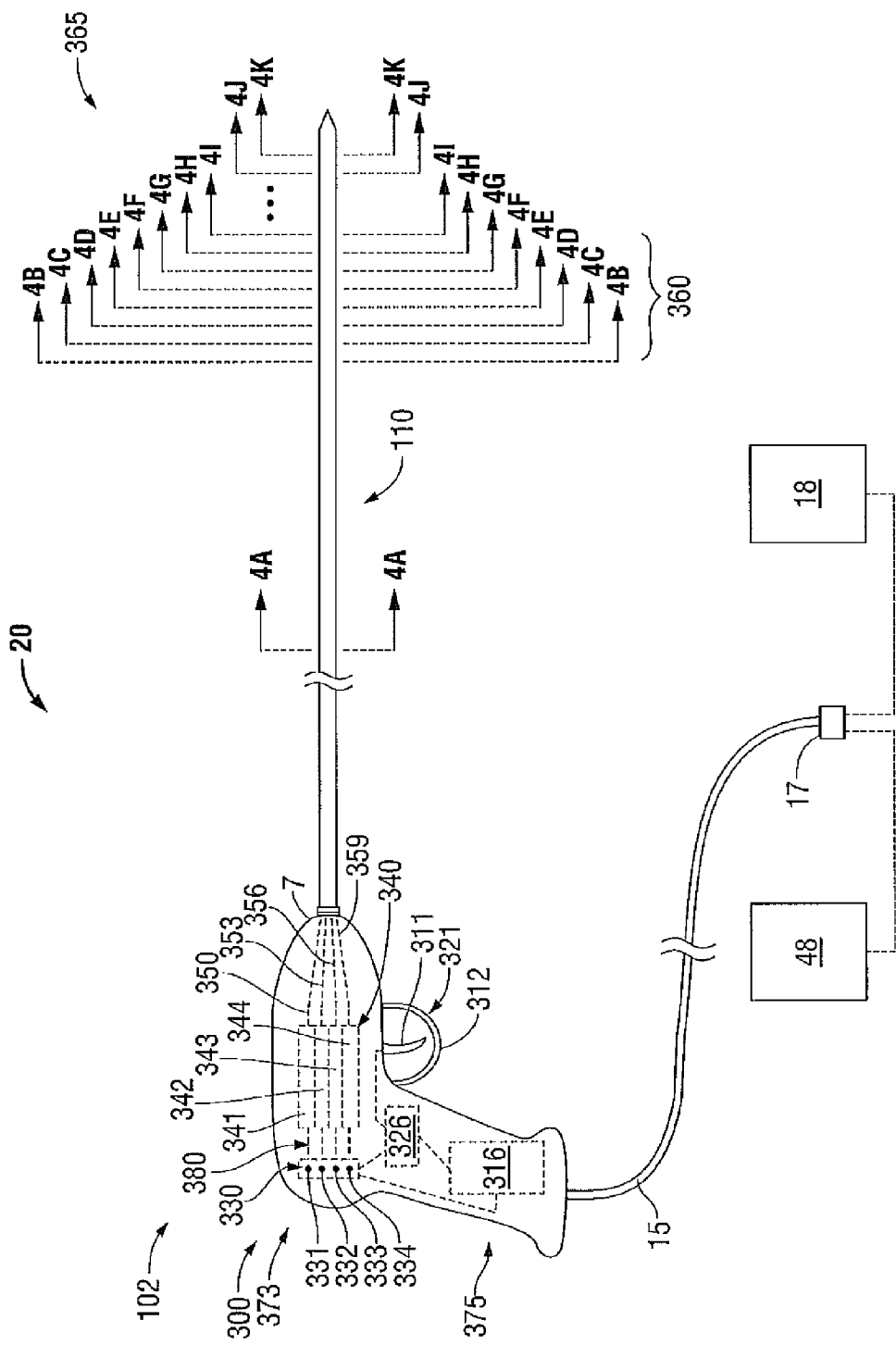
FIG. 3 is a schematic diagram of an ablation system including an embodiment of an ablation device capable of utilizing an exothermic chemical reaction for applying ablative thermal energy to tissue in accordance with an embodiment of the present disclosure.
Figure 5:
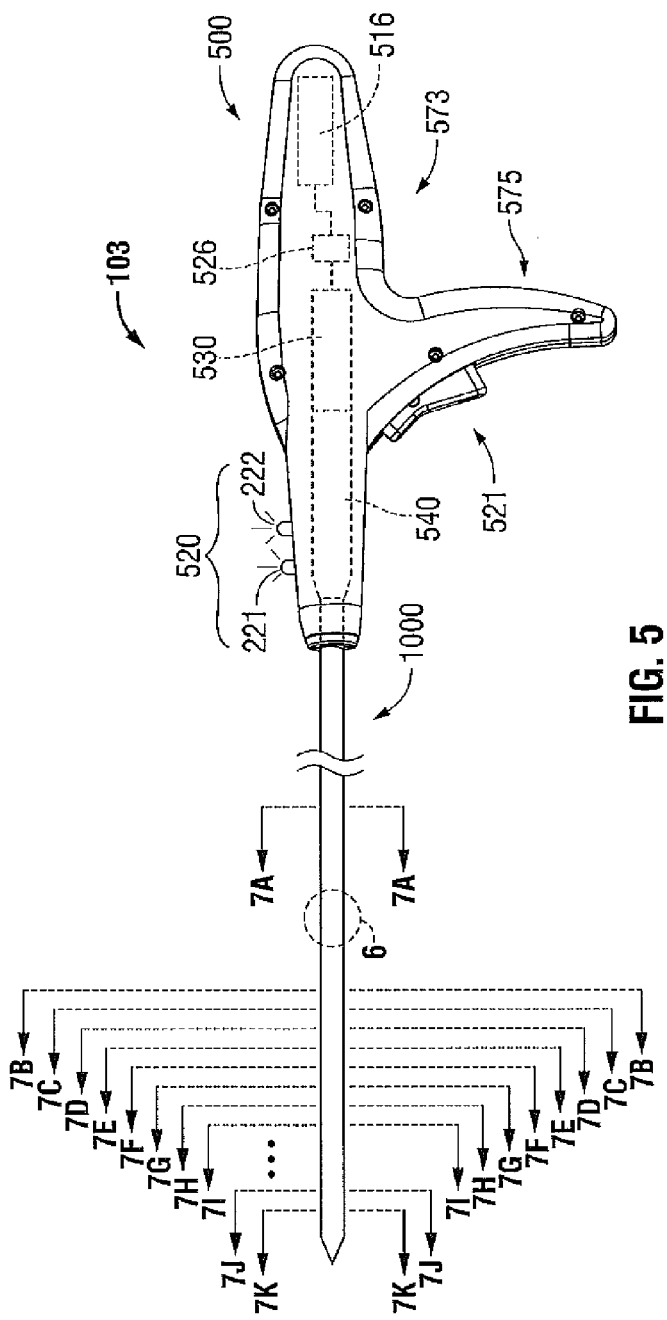
FIG. 5 is a perspective view of another embodiment of an ablation device capable of utilizing an exothermic chemical reaction for applying ablative thermal energy to tissue in accordance with the present disclosure.

It is envisioned and within the scope of the present disclosure that any combination of battery cells, a battery pack, fuel cell and/or high-energy capacitor may be used to provide power to the ablation device (e.g., 101, 102 and 103 shown in FIGS. 2, 3 and 5, respectively). For example, capacitors may be used in conjunction with a battery pack. In such case, the capacitors may discharge a burst of power to provide energy more quickly than batteries are capable of providing, as batteries are typically slow-drain devices from which current cannot be quickly drawn. It is envisioned that batteries may be connected to the capacitors to charge the capacitors.

A battery pack may include at least one disposable battery. In such case, the disposable battery may be between about 9 volts and about 30 volts, and may be useful as a primary power source for a processor unit (e.g., 226 shown in FIG. 2). In some embodiments, a transmission line (e.g., 15 shown in FIG. 3) is provided to connect the ablation device (e.g., 102 shown in FIG. 3) to a line source voltage or external power source (e.g., 48 shown in FIG. 3), in which case a battery pack may be used as a backup power source.

FIG. 1 shows a schematic of a heat-generating system 10 for use in carrying out an exothermic reaction to produce thermal energy (shown generally as "H" in FIG. 1). Heat-generating system 10 generally includes a processor unit 26, a user interface 70 operably associated with the processor unit 26, and an exothermic reaction unit 11 configured to selectively carry out an exothermic chemical reaction in which thermal energy is released.

Exothermic reaction unit 11 includes one or more controllable actuators (e.g., 31, 32 and 33) operably associated with one or more fluid reservoirs (e.g., 41, 42 and 43) and/or one or more fluid flow paths (e.g., 131, 132 and 133), and may be operably associated with the processor unit 26. The actuators may be of any suitable type. Examples of types of actuators that may be suitable include hydraulic actuators, pneumatic actuators, and electro-mechanical actuators. Processor unit 26 is communicatively associated with the one or more actuators and adapted to generate an electric signal for controlling an operation of the one or more actuators, e.g., to supply force and motion to position one or more moveable members (e.g., 380 shown in FIG. 3) operably associated therewith. Logic associated with one or more actuators may control an operation of the actuator in response to a user-initiated action. In some embodiments, the user interface 70 includes a user-operable switch (e.g., 21 shown in FIG. 2) that is electrically coupled to the processor unit 26. A user-operable switch may additionally, or alternatively, be mechanically coupled to one or more actuators for selectively generating a fluid flow when mechanical force is applied thereto.

In some embodiments, the user interface 70 may include a fluid-flow monitoring system adapted to monitor and/or regulate the pressure and/or flow rate of fluid and capable of generating a signal indicative of an abnormal fluid-flow condition. User interface 70 may additionally, or alternatively, include audio and/or visual indicator devices. User feedback may be included in the form of pulsed patterns of light, acoustic feedback (e.g., buzzers, bells or beeps that may be sounded at selected time intervals), verbal feedback, and/or haptic vibratory feedback (such as an asynchronous motor or solenoids), for example.

Processor unit 26 is operably associated with a power source 16, e.g., a battery pack. Processor unit 26 may include any type of computing device, computational circuit, or any type of processor or processing circuit capable of executing a series of instructions that are stored in a memory (not shown) of the processor unit 26. The series of instructions may be transmitted via propagated signals for execution by the processor unit 26 for performing the functions described herein and to achieve a technical effect in accordance with the present disclosure. It is envisioned and within the scope of the present disclosure that the heat-generating system 10 may include a temperature sensor, e.g., a thermocouple, which may be monitored by the processor unit 26.

Heat-generating system 10 according to an embodiment of the present disclosure includes a first actuator 31 operably associated with a first fluid flow path 131, a second actuator 32 operably associated with a second fluid flow path 132, and a third actuator 33 operably associated with a third fluid flow path 133. First fluid flow path 131 is in fluid communication with a first reservoir 41. First reservoir 41 is capable of containing a quantity of a first fluid "F1", and may be capable of holding the first fluid "F1" under pressure. Second fluid flow path 132 is in fluid communication with a second reservoir 42. Second reservoir 42 is capable of containing a quantity of a second fluid "F2", and may be capable of holding the second fluid "F2" under pressure. Third fluid flow path 133 is in fluid communication with a third reservoir 43, which is capable of containing a quantity of a third fluid "F3".

First fluid "F1" and the second fluid "F2" may include any reagent or reactant suitable for use in an exothermic reaction to produce thermal energy for treating tissue, e.g., ablative thermal energy. The portion of the first fluid "F1" that serves as a reactant (e.g., readable with the second fluid "F2" to produce an exothermic reaction) may be referred to herein as a "first reactant portion", and the portion of the second fluid "F2" that serves as a reactant (e.g., reactable with the first fluid "F1" to produce an exothermic reaction) may be referred to herein as a "second reactant portion".

In some embodiments, the first fluid "F1" may be an acid and the second fluid "F2" may be a base. It will be appreciated that the first fluid "F1" may be a base and the second fluid "F2" may be an acid. Third fluid "F3" may include products of a reaction, e.g., an acid-base reaction, between the first fluid "F1" and the second fluid "F2". In some embodiments, the third fluid "F3" may be a coolant fluid, e.g., water or saline.

In some embodiments, the first fluid "F1" includes a strong acid, and the second fluid "F2" may include a weak base. Substances that ionize 95% or better in water are usually referred to as strong acids. Examples of strong acids include hydrochloric acid (HCl), hydrobromic acid (HBr), hydroiodic acid (HI), sulfuric acid ($H_2SO_4$), nitric acid ($HNO_3$), chloric acid ($HClO_3$) and perchloric acid ($HClO_4$). Examples of weak bases include alanine ($C_5H_5NH_2$), ammonia ($NH_3$), methylamine ($CH_3NH_2$) and pyridine ($C_5H_5N$). In some embodiments, the second fluid "F2" includes a strong base, and the first fluid "F1" may include a weak acid. Examples of strong bases include potassium hydroxide (KOH), barium hydroxide ($Ba(OH)_2$), caesium hydroxide (CsOH), sodium hydroxide (NaOH), strontium hydroxide ($Sr(OH)_2$), calcium hydroxide ($Ca(OH)_2$), lithium hydroxide (LiOH), rubidium hydroxide (RbOH) and magnesium hydroxide ($Mg(OH)_2$). Examples of weak acids include acetic acid ($CH_3COOH$) and oxalic acid ($H_2C_2O_4$).

In some embodiments, the first fluid "F1" includes HCl and the second fluid "F2" includes any suitable metal oxides reactable with HCl to produce an exothermic reaction. In one embodiment, the first fluid "F1" includes hydrochloric acid (HCl), the second fluid "F2" includes sodium hydroxide (NaOH), and the third fluid "F3" includes water ($H_2O$) and salt (NaCl) produced by the HCl+NaOH reaction. It is envisioned and within the scope of the present disclosure that other chemical compounds and substances reactable to produce an exothermic reaction may be utilized by the presently disclosed heat-generating system 10. For example, other substances reactable to produce an exothermic reaction may include $Na(s)+0.5Cl_2(s) \rightarrow NaCl(s)$+heat in an amount of 411 kilojoules (kJ) per mole of NaCl produced.

As illustrated in FIG. 1, the flow of the first fluid "F1" through the first fluid flow path 131 and the flow of the second fluid "F2" through the second fluid flow path 132 merge at a mixing junction 60. Upon mixing of the first and second fluids "F1" and "F2", a chemical reaction occurs that releases thermal energy (shown generally as "H" in FIG. 1), e.g., sufficient to cause localized tissue heating around a portion 133a of the third fluid flow path 133. In some embodiments, a quantity of a first reactant portion may be mixed with a quantity of a second reactant portion to control the reaction rate and/or provide a temperature-controlled ablation procedure, e.g., by controlling the range of temperature between minimum and maximum temperature and/or the rate of change of temperature. In some embodiments, the first reactant portion and/or the second reactant portion may be limited to a quantity that produces only the desired amount of heat. In some embodiments, the quantity of the first reactant portion is exceeded by the quantity of the second reactant portion. For example, in the case of $Na+0.5Cl_2 \rightarrow NaCl$, if the quantity of sodium is doubled while the quantity of chlorine is not increased, such that $2Na+0.5Cl_2 \rightarrow NaCl+Na$, then the quantity of chlorine limits the reaction.

FIG. 2 shows an ablation device 101 configured to utilize an exothermic chemical reaction for applying ablative thermal energy to tissue according to an embodiment of the present disclosure that includes an applicator or probe 100. Ablation device 101 generally includes a handle assembly 200 including a grip portion 275 and a handle body 273 configured to support the probe 100 at a distal end 3 thereof. Handle assembly 200, according to various embodiments, may be fabricated from metals, plastics, ceramics, composites, e.g., plastic-metal or ceramic-metal composites, or other materials. The shape and size of the handle assembly 200 and the probe 100 may be varied from the configuration depicted in FIG. 2.

Probe 100 generally includes one or more fluid flow paths (e.g., 52, 55 and 58 shown in FIG. 2) configured to allow mixing and/or delivery of fluid to a heat-transfer portion 12 of the probe 100. Probe 100 may be configured to be detachably mountable to the distal end 3 of handle body 273, and may be disposable. In some embodiments, the ablation device 101 may be configured to allow for replacement of the cartridge unit 40 and/or the probe 100.

Probe 100, or portion thereof, includes a thermally-conductive material, such as, for example, copper, stainless steel, titanium, titanium alloys such as nickel-titanium and titanium-aluminum-vanadium alloys, aluminum, aluminum alloys, tungsten carbide alloys or combinations thereof. In some embodiments, the probe 100, or portion thereof, may be provided with an outer jacket (not shown) disposed at least partially thereabout. The outer jacket may be formed of any suitable material, such as, for example, polymeric or ceramic materials. The outer jacket may be applied by any suitable method, such as, for example, heat shrinking, overmolding, coating, spraying dipping, powder coating, baking and/or film deposition.

Heat-transfer portion 12 of the probe 100 may be formed of a high thermally conductive material, e.g., aluminum. Heat-transfer portion 12 may terminate in a sharp tip 23 to allow for insertion into tissue with minimal resistance. Heat-transfer portion 12 may include other shapes, such as, for example, a tip 23 that is rounded, flat, square, hexagonal, or cylindroconical.

During an ablation procedure, the probe 100 is inserted into or placed adjacent to tissue and thermal energy is supplied thereto. Probe 100 may be placed percutaneously or surgically, e.g., using conventional surgical techniques by surgical staff. A clinician may pre-determine the length of time that thermal energy is to be applied. Application duration may depend on a variety of factors such as applicator design, number of applicators used simultaneously, tumor size and location, and whether the tumor was a secondary or primary cancer. The duration of thermal energy application using the probe 100 may depend on the progress of the heat distribution within the tissue area that is to be destroyed and/or the surrounding tissue. Through limitation of the quantity of a reactant, the amount of thermal energy generated may be controlled. The rate of flow of the reactant and/or its concentration may be adjustable to ensure that only a predetermined amount of energy is available during one application. Thermal probes may also be used to monitor and measure temperature of the reaction product. In some embodiments, a feedback loop may be used to allow adjustment of the rate of flow and/or concentration of the reactant(s) based on the measured temperature of the reaction product.

Handle body 273 may include a retaining mechanism 14 configured to detachably hold the probe 100. In some embodiments, the retaining mechanism 14 includes a retainer member that is movable between at least an engagement position and a released position. In some embodiments, the ablation device 101 may include a user-operable switch mechanically coupled to the handle body 273, e.g., a push button, operable to move the retaining mechanism 14 from an engagement position, in which the retainer member is engaged with a connector member of the probe 100, to a released position, in which the retainer member is disengaged from the connector member of the probe 100.

Ablation device 101 according to some embodiments includes a self-contained, power unit 216 and a processor unit 226 that is electrically coupled to the power unit 216. Ablation device 101 may be configured to allow for user replacement of the power unit 216. Power unit 216 may be disposed within the handle assembly 200, e.g., within the grip portion 275 and/or the handle body 273. For example, the handle assembly 200 may be equipped with a battery chamber assessable through a manageable lid. This may include a screw fastener, snap, or other suitable fasting closure means. Power unit 216 may include one or more batteries, which may be a rechargeable type such as a nickel cadmium battery. Ablation device 101 may additionally, or alternatively, be operably coupled to a line source voltage or external power source (e.g., 48 shown in FIG. 3). Processor unit 226 is similar to the processor unit 26 of FIG. 1 and further description thereof is omitted in the interests of brevity.

Ablation device 101 includes a user-operable trigger mechanism or switch 21 that is operably associated with the processor unit 226. Processor unit 226 may control an operation of an actuator unit 30 in response to the activation of the switch 21. In an embodiment, the user-operable switch 21 includes a trigger 211 located within a trigger guard 212. The shape and size of the trigger 211 and the trigger guard 212 may be varied from the configuration depicted in FIG. 2. Switch 21 may utilize any suitable switch configuration. Examples of switch configurations that may be suitable for use with the ablation device 101 include, but are not limited to, pushbutton, toggle, rocker (e.g., 521 shown in FIG. 5), tactile, snap, rotary, slide, and thumbwheel. As an alternative to, or in addition to, the switch 21, the ablation device 101 may include voice input technology, which may include hardware and/or software incorporated in the processor unit 226, or a separate digital module connected to the processor unit 226. The voice input technology may include voice recognition, voice activation, voice rectification, and/or embedded speech.

Ablation device 101 includes a first fluid-flow path 50 and a second fluid-flow path 53, and may include a third fluid-flow path 56. In some embodiments, a portion 51 of the first fluid-flow path 50, a portion 54 of the second fluid-flow path 53, and a portion 57 of the third fluid-flow path 56 are disposed within the handle assembly 200, and a portion 52 of the first fluid-flow path 50, a portion 55 of the second fluid-flow path 53, and a portion 58 of the third fluid-flow path 56 are disposed within the probe 100. Ablation device 101 may be provided with one or more connectors configured to releasably couple the portions 51, 52 of the first fluid-flow path 50, the portions 54, 55 of the second fluid-flow path 53, and/or the portions 57, 58 of the third fluid-flow path 56.

Ablation device 101 includes an actuator unit 30 that is operably associated with a cartridge unit 40. Actuator unit 30 may additionally be operably associated with the power unit 216 and/or other power source. Actuator unit 30 generally includes one or more actuators. In some embodiments, the processor unit 226 is communicatively associated with the one or more actuators and adapted to generate an electric signal for controlling an operation of the one or more actuators. In an embodiment, the actuator unit 30 includes a first actuator 231 operably associated with a first reservoir 241, a second actuator 232 operably associated with a second reservoir 242, and a third actuator 233 operably associated with a third reservoir 243. First, second and third actuators 231, 232 and 233 and the first, second and third reservoirs 241, 242 and 243 are similar to the first, second and third actuators 31, 32 and 33 and the first, second and third reservoirs 41, 42 and 43, respectively, shown in FIG. 1, and further description thereof is omitted in the interests of brevity.

FIG. 3 shows an ablation system 20 including an embodiment of an ablation device 102 capable of utilizing an exothermic chemical reaction for applying ablative thermal energy to tissue in accordance with the present disclosure. Ablation device 102 generally includes a handle assembly 300 including a grip portion 375 and a handle body 373 configured to support an applicator or probe 110 at a distal end 7 thereof. It will be understood, however, that other probe embodiments (e.g., 103 shown in FIG. 5) may be used.

In some embodiments, the ablation device 102 is electrically connected via a transmission line 15 to a connector 17, which may further operably connect the ablation device 102 to a line source voltage or external power source 48. Transmission line 15 may additionally, or alternatively, provide a conduit (not shown) configured to provide coolant from a coolant source 18 to the probe 110.

During a procedure, e.g., an ablation procedure, using the electrosurgical system 20, the probe 110 is inserted into or placed adjacent to tissue and thermal energy is supplied thereto. Ultrasound or computed tomography (CT) guidance may be used to accurately guide the probe 110 into the area of tissue to be treated. A plurality of probes 110 may be placed in variously-arranged configurations to substantially simultaneously ablate a target tissue region, making faster procedures possible. Multiple probes 110 may be used to synergistically create a large ablation or to ablate separate sites simultaneously. Probe 110 generally includes one or more fluid flow paths configured to allow mixing and/or delivery of fluid to a heat-transfer portion 365 of the probe 110.

Ablation device 102 includes a processor unit 326, which may be operably associated with the power unit 316 and/or the external power source 48. Processor unit 326 is similar to the processor unit 26 of FIG. 1 and further description thereof is omitted in the interests of brevity.

Ablation device 102 includes an actuator unit 330. Actuator unit 330 may include any suitable number of actuators. Actuator unit 330 is operably associated with a cartridge unit 340. Probe 100 generally includes a plurality of fluid-flow paths in fluid communication with the cartridge unit 340 via a plurality of fluid-flow paths (e.g., 350, 353, 356 and 359) disposed within the handle assembly 300. Actuator unit 330 according to an embodiment of the present disclosure includes a first actuator 331 operably associated with a first fluid flow path 350, a second actuator 332 operably associated with a second fluid flow path 353, a third actuator 333 operably associated with a third fluid flow path 356, and a fourth actuator 334 operably associated with a fourth fluid flow path 359.

Cartridge unit 340 includes a first reservoir 341, a second reservoir 342 and a third reservoir 343, and may include a fourth reservoir 344. In some embodiments, the cartridge unit 340 is similar to the cartridge unit 40 of FIG. 1, except that the cartridge unit 340 includes a fourth reservoir 344 that is configured to contain a coolant fluid, e.g., water, in fluid communication with a fourth fluid-flow path 359.

Figure 4A:
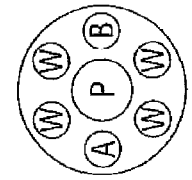
FIG. 4A is a cross-sectional view of a proximal portion of the probe of the ablation device of FIG. 3 taken along section lines 4A-4A according to an embodiment of the present disclosure.
Figure 4B:
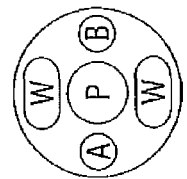
FIGS. 4B through 4I are cross-sectional views of a fluid-mixing portion of the probe of the ablation device of FIG. 3 taken along section lines 4B-4B through 4I-4I, respectively, according to an embodiment of the present disclosure.
Figure 4C:
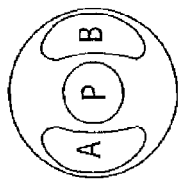
Figure 4D:
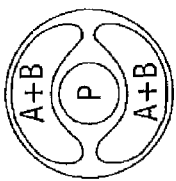
Figure 4E:
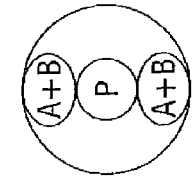
Figure 4F:
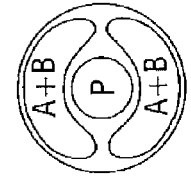
Figure 4G:
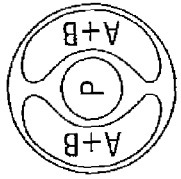
Figure 4H:
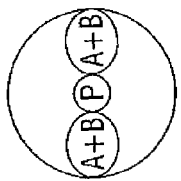
Figure 4I:
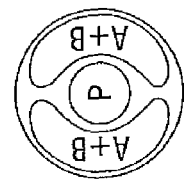
Figure 4J:
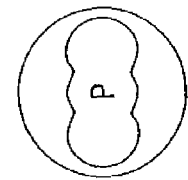
FIGS. 4J and 4K are cross-sectional views of a distal portion of the probe of the ablation device of FIG. 3 taken along section lines 4J-4J and 4K-4K, respectively, according to an embodiment of the present disclosure.
Figure 4K:
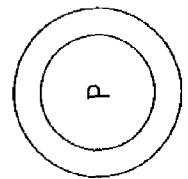

As shown in FIG. 4A, a proximal portion of the probe 110 may be provided with a fluid-flow path for conveying an acid, A, flow therein; a fluid-flow path for conveying a base, B, flow therein; a plurality of fluid-flow paths for conveying water, W, flow therein; and a fluid-flow path for conveying flow of a product, P, e.g., formed during an exothermic chemical reaction. FIGS. 4B through 4I show an embodiment of fluid-flow paths forming a fluid-mixing portion 360 (shown in FIG. 3) of the probe 110 in accordance with the present disclosure. An embodiment of a fluid-flow path for conveying flow of the product, P, within a distal portion of the probe 110 is shown in FIGS. 4J and 4K. The shape, size and relative spacing of the fluid-flow paths of the probe 110 may be varied from the configurations depicted in FIGS. 4A through 4K.

Figure 7A:
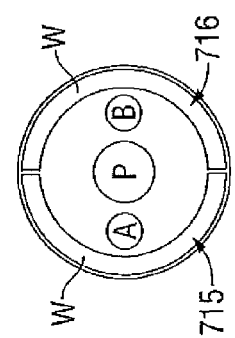
FIG. 7A is a cross-sectional view of a proximal portion of the probe of the ablation device of FIG. 5 including a cooling jacket disposed thereabout taken along section lines 7A-7A according to an embodiment of the present disclosure.
Figure 7D:
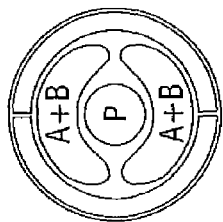
FIGS. 7B through 7H are cross-sectional views of a fluid-mixing portion of the probe of the ablation device of FIG. 5 including a cooling jacket disposed thereabout taken along section lines 7B-7B through 7H-7H, respectively, according to an embodiment of the present disclosure.
Figure 7B:
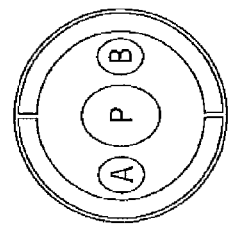
Figure 7C:
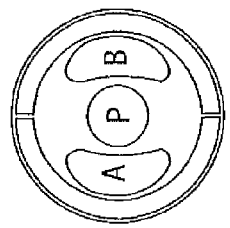
Figure 7E:
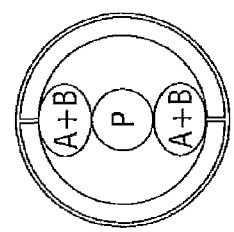
Figure 7F:
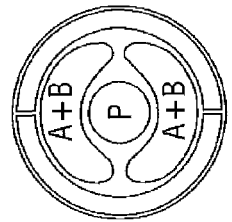
Figure 7G:
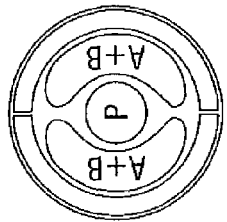
Figure 7H:
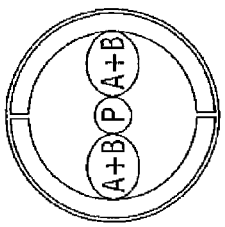
Figure 7I:
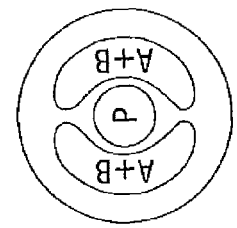
FIGS. 7I through 7K are cross-sectional views of a heat-transfer portion of the probe of the ablation device of FIG. 5 taken along section lines 7I-7I through 7K-7K, respectively, according to an embodiment of the present disclosure.
Figure 7J:
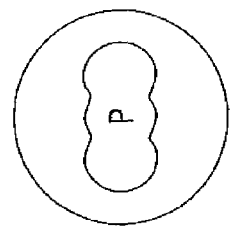
Figure 7K:
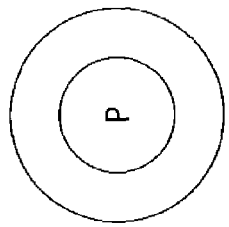

In other embodiments, the probe 110, or portion thereof, may be provided with an outer coolant chamber (e.g., 715 and 716 shown in FIG. 7A). Additionally, the probe 110 may include coolant inflow and outflow ports (not shown) to facilitate the flow of coolant into, and out of, the coolant chamber. Examples of coolant chamber and coolant inflow and outflow port embodiments are disclosed in commonly assigned U.S. patent application Ser. No. 12/401,268 filed on Mar. 10, 2009, entitled "COOLED DIELECTRICALLY BUFFERED MICROWAVE DIPOLE ANTENNA", and U.S. Pat. No. 7,311,703, entitled "DEVICES AND METHODS FOR COOLING MICROWAVE ANTENNAS".

FIG. 5 shows an ablation device 103 capable of utilizing an exothermic chemical reaction for applying ablative thermal energy to tissue according to an embodiment of the present disclosure. Ablation device 103 generally includes a handle assembly 500 including a grip portion 575 and a handle body 573 configured to support an applicator or probe 1000 at a distal end thereof. Handle assembly 500 includes a controller 526, a switch 521, and an indicator unit 520 including one or more light-emitting elements (e.g., 221 and 222). The shape and size of the handle assembly 500 and the probe 1000 may be varied from the configuration depicted in FIG. 5.

Switch 521 may be any suitable switch that generally fulfills the purpose of switching electrical circuits on and off or switching over from one electrical circuit to another. In the embodiment illustrated in FIG. 5, the switch 521 is a rocker-type switch that generally includes two wing portions projecting from opposite sides of a rotational axis for alternatingly engaging depressible operators of the switch 521. The shape, size and location of the switch 521 may be varied from the configuration depicted in FIG. 5

In an embodiment, the indicator unit 520 may include a first LED 221 and a second LED 222. In some embodiments, a change in color of the first LED 221 and/or the second LED 222 may be used to indicate a user-initiated action and/or to signal temperature-related information. Indicator unit 520 may be used to signal the occurrence of an abnormal fluid-flow condition, or other condition, e.g., low-battery condition.

Ablation device 103 includes an actuator unit 530 that is operably associated with a cartridge unit 540. Cartridge unit 540 includes one or more reservoirs configured to contain fluids therein, e.g., three or four reservoirs, and may be formed of any suitable material. Cartridge unit 540 may be adapted to be removeably coupleable to an actuator 540. The reservoirs may have any suitable size, shape and capacity or storage volume. In an embodiment, the cartridge unit 540 includes a first reservoir configured to contain a first fluid, e.g., an acid, a second reservoir configured to contain a second fluid, e.g., a base, a third reservoir configured to contain a third fluid, e.g., water or saline, and a fourth reservoir configured to receive a flow of a fourth fluid, e.g., water and/or a product of an exothermic chemical reaction. The capacity of the fourth reservoir may be sufficient to allow the fourth reservoir to receive and contain the first, second and/or third fluid therein. In various embodiments, the ablation device 103 may be configured to allow for replacement of the cartridge unit 540 and/or the probe 1000.

Figure 6:
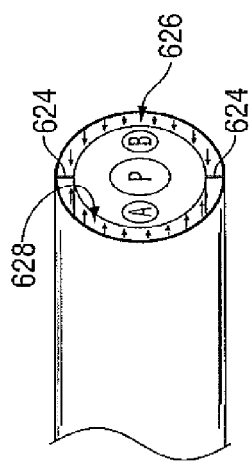
FIG. 6 is partial, cross-sectional side perspective view of the indicated area of detail of FIG. 5 according to an embodiment of the present disclosure.

Probe 1000 generally includes a plurality of fluid-flow paths in fluid communication with the cartridge unit 540. As shown in FIG. 6, a proximal portion of the probe 1000 may be provided with a fluid-flow path for conveying an acid, A, flow therein, a fluid-flow path for conveying a base, B, flow therein, a fluid-flow path for conveying flow of a product, P, e.g., formed during an exothermic chemical reaction, and an outer coolant chamber including first and second portions 626 and 628 for conveying water flow therein.

FIG. 8 shows an apparatus capable of generating fluid flow by controlling the position of one or more pistons or plungers (e.g., "P1", "P2" and "P3") within one or more fluid reservoirs (e.g., 541, 542 and 543) of a cartridge unit 540 according to an embodiment of the present disclosure. Cartridge unit 540 is operably associated with an actuator unit 530. Actuator unit 530 is operably associated with a processor unit 26, and may include any number of actuators of any suitable type, e.g., electromechanical actuators. Actuator unit 530 may include stepper motors and various servo motors, coupled with gears. In an embodiment, a first plunger "P1" is mechanically coupled to a first actuator 531 through a mechanical coupling, a second plunger "P2" is mechanically coupled to a second actuator 532 through a mechanical coupling, and a third plunger "P3" is mechanically coupled to a third actuator 533 through a mechanical coupling.

Under the control of the processor unit 26, the first actuator 531 causes the first plunger "P1" to expel a volume of a first fluid "F1" contained within the first reservoir 541, and the second actuator 532 causes the second plunger "P2" to expel a volume of a second fluid "F2" contained within the second reservoir 542. In an alternative embodiment, one actuator may be mechanically coupled to both the first and second plungers "P1" and "P2", instead of the first and second actuators 531 and 532 shown in FIG. 8. In some embodiments, under the control of the processor unit 26, the third actuator 533 causes the third plunger "P3" to expel a volume of a third fluid "F3", e.g., water, and/or to collect a volume of a product formed during an exothermic chemical reaction.

Hereinafter, methods of delivering thermal energy to tissue are described with reference to FIGS. 9 and 10. It is to be understood that the steps of the methods provided herein may be performed in combination and in a different order than presented herein without departing from the scope of the disclosure.

Figure 9:
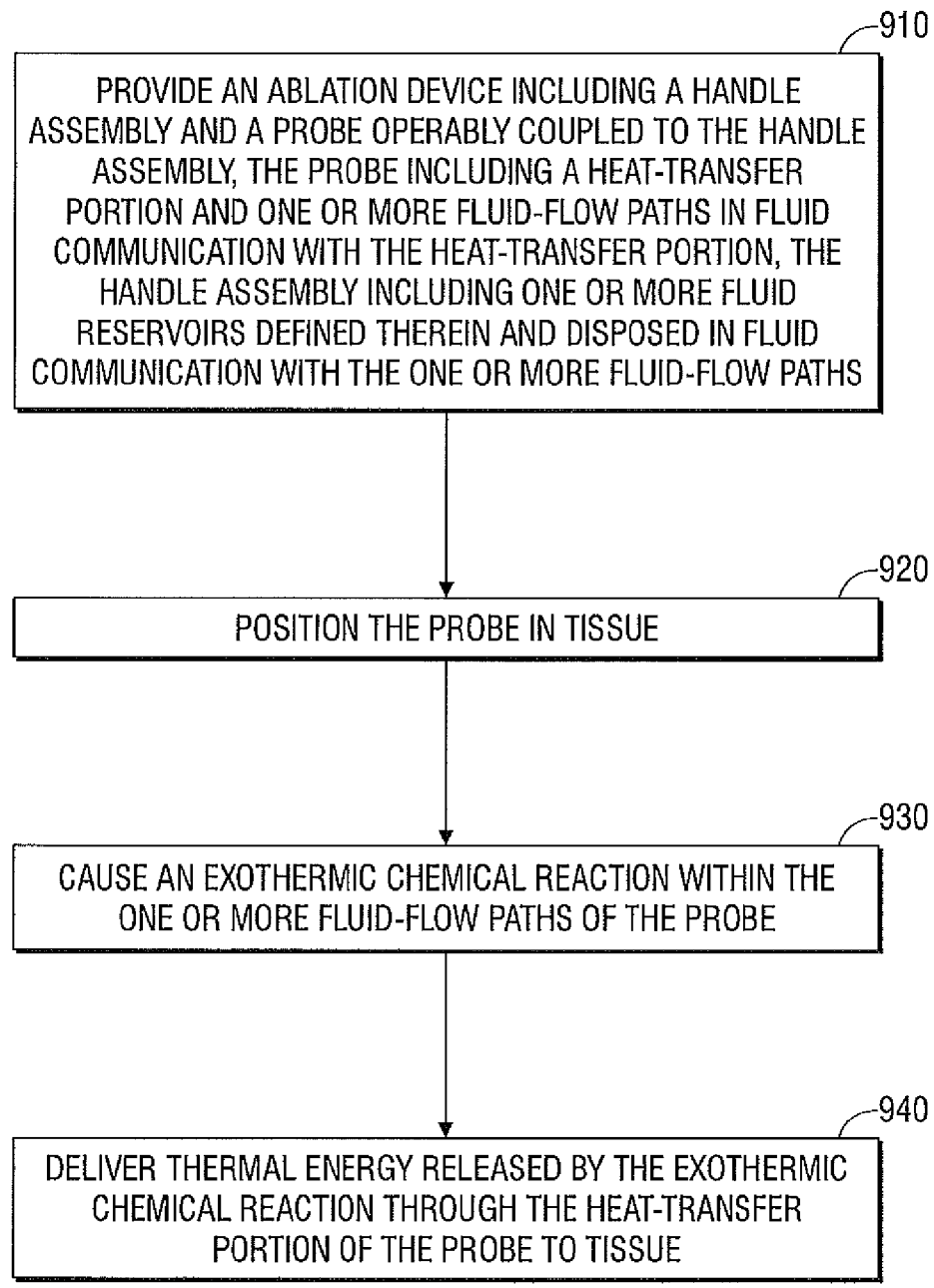
FIG. 9 is a flowchart illustrating a method of ablating tissue according to an embodiment of the present disclosure.

FIG. 9 is a flowchart illustrating a method of delivering thermal energy to tissue according to an embodiment of the present disclosure. In step 910, an ablation device (e.g., 101 shown in FIG. 2) is provided. The ablation device (e.g., 101 shown in FIG. 2) includes a handle assembly (e.g., 200 shown in FIG. 2) and a probe (e.g., 100 shown in FIG. 2)

operably coupled to the handle assembly. The probe (e.g., 101 shown in FIG. 2) includes a heat-transfer portion (e.g., 12 shown in FIG. 2) and one or more fluid-flow paths (e.g., 50, 53 and 56 shown in FIG. 2) in fluid communication with the heat-transfer portion. The handle assembly (e.g., 200 shown in FIG. 2) includes one or more fluid reservoirs (e.g., 241, 242 and 243 shown in FIG. 2) in fluid communication with the one or more fluid-flow paths (e.g., 50, 53 and 56 shown in FIG. 2).

In step 920, the probe (e.g., 100 shown in FIG. 2) is positioned in tissue. The probe may be inserted directly into tissue, inserted through a lumen, e.g., a vein, needle or catheter, placed into the body during surgery by a clinician, or positioned in the body by other suitable methods.

In step 930, an exothermic chemical reaction is caused within the one or more fluid-flow paths (e.g., 52, 55 and 58 shown in FIG. 2) of the probe (e.g., 100 shown in FIG. 2). The step 930 of causing an exothermic chemical reaction within the one or more fluid-flow paths (e.g., 350, 353, 356 and 359 shown in FIG. 3) of the probe (e.g., 110 shown in FIG. 3) may include causing fluid flow of an acid and a base to a mixing junction (e.g., 360 shown in FIG. 3) of the probe (e.g., 110 shown in FIG. 3). In some embodiments, the acid may be selected from the group consisting of hydrochloric acid (HCl), hydrobromic acid (HBr), hydroiodic acid (HI), sulfuric acid ($H_2SO_4$), nitric acid ($HNO_3$), chloric acid ($HClO_3$) and/or perchloric acid ($HClO_4$). In some embodiments, the base may be selected from the group consisting of potassium hydroxide (KOH), barium hydroxide ($Ba(OH)_2$), caesium hydroxide (CsOH), sodium hydroxide (NaOH), strontium hydroxide ($Sr(OH)_2$), calcium hydroxide ($Ca(OH)_2$), lithium hydroxide (LiOH), rubidium hydroxide (RbOH) and/or magnesium hydroxide ($Mg(OH)_2$).

In step 940, thermal energy released by the exothermic chemical reaction is delivered through the heat-transfer portion (e.g., 12 shown in FIG. 2) of the probe (e.g., 100 shown in FIG. 2) to tissue. Products of the exothermic reaction may be directed away from the heat-transfer portion (e.g., 12 shown in FIG. 2) via a fluid-flow path (e.g., 56 shown in FIG. 2) in fluid communication with a fluid reservoir (e.g., 243 shown in FIG. 2) disposed in the handle assembly (e.g., 200 shown in FIG. 2).

Figure 10:
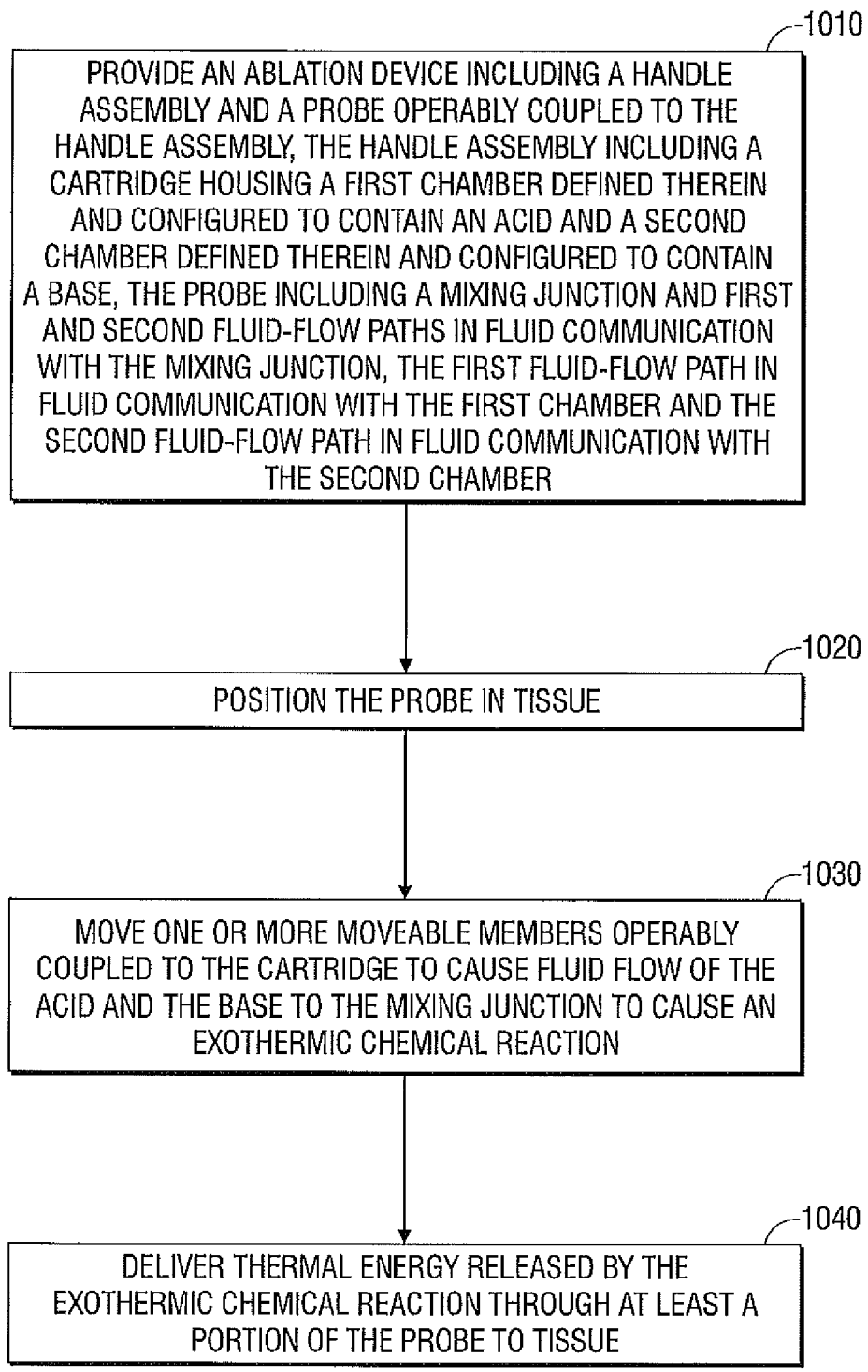
FIG. 10 is a flowchart illustrating a method of ablating tissue according to another embodiment of the present disclosure.

FIG. 10 is a flowchart illustrating a method of delivering thermal energy to tissue according to an embodiment of the present disclosure. In step 1010, an ablation device (e.g., 102 shown in FIG. 3) is provided. The ablation device (e.g., 102 shown in FIG. 3) includes a handle assembly (e.g., 300 shown in FIG. 3) and a probe (e.g., 110 shown in FIG. 3) extending from a distal end (e.g., 7 shown in FIG. 3) of the handle assembly. The handle assembly includes a cartridge unit (e.g., 340 shown in FIG. 3) housing a first chamber (e.g., 341 shown in FIG. 3) containing a first fluid, e.g., an acid, and a second chamber (e.g., 342 shown in FIG. 3) containing a second fluid, e.g., a base. The probe (e.g., 110 shown in FIG. 3) includes a mixing junction (e.g., 360 shown in FIG. 3) and first and second fluid-flow paths (e.g., 350 and 353 shown in FIG. 3) in fluid communication with the mixing junction. The first fluid-flow path (e.g., 350 shown in FIG. 3) is in fluid communication with the first chamber (e.g., 341 shown in FIG. 3), and the second fluid-flow path (e.g., 353 shown in FIG. 3) is in fluid communication with the second chamber (e.g., 342 shown in FIG. 3).

In step 1020, the probe (e.g., 110 shown in FIG. 3) is positioned in tissue. Ultrasound, computed tomography (CT) guidance, or other guidance may be used to accurately guide the probe into the area of tissue to be treated.

In step 1030, one or more moveable members (e.g., 380 shown in FIG. 3) operably coupled to the cartridge unit (e.g., 340 shown in FIG. 3) are moved to cause fluid flow of the acid and the base to the mixing junction (e.g., 360 shown in FIG. 3) to cause an exothermic chemical reaction.

In step 1030, thermal energy released by the exothermic chemical reaction is delivered through at least a portion of the probe (e.g., 110 shown in FIG. 3) to tissue.

The above-described tissue ablation devices and system including the same are capable of directing thermal energy to heat, ablate and/or coagulate tissue without the use of electromagnetic radiation. The capability to provide ablative thermal heat without the use of electromagnetic radiation may enhance device portability and location independence, and may help to facilitate improved patient accessibility to hyperthermic treatments.

Although embodiments have been described in detail with reference to the accompanying drawings for the purpose of illustration and description, it is to be understood that the inventive processes and apparatus are not to be construed as limited thereby. It will be apparent to those of ordinary skill in the art that various modifications to the foregoing embodiments may be made without departing from the scope of the disclosure.

What is claimed is:

1. A method for ablating tissue, the method comprising:
positioning an ablation device adjacent tissue to be treated, the ablation device including:
a probe including a heat-transfer portion in communication with at least one of a first fluid-flow path and a second fluid-flow path, the first fluid-flow path in communication with a first fluid reservoir, the second fluid-flow path in communication with a second fluid reservoir, and the heat-transfer portion in fluid communication with a third fluid reservoir,
contacting a first fluid, from within the first fluid reservoir, with a second fluid, from within the second fluid reservoir, to generate an exothermic reaction;
receiving a product of the exothermic reaction in the heat-transfer portion;
delivering thermal energy released from the exothermic reaction to the tissue to be treated; and
receiving the product of the exothermic reaction in the third fluid reservoir.

2. The method of claim 1, further comprising expelling the first fluid from the first fluid reservoir, through the first fluid-flow path, and into the heat-transfer portion.

3. The method of claim 2, wherein expelling the first fluid includes actuating a first plunger associated with the first fluid reservoir.

4. The method of claim 3, further comprising generating an electric signal with a controller unit, the electric signal controlling actuation of the first plunger.

5. The method of claim 1, further comprising expelling the second fluid from the second fluid reservoir, through the second fluid-flow path, and into the heat-transfer portion.

6. The method of claim 5, wherein expelling the second fluid includes actuating a second plunger associated with the second fluid reservoir.

7. The method of claim 1, further comprising engaging a mechanical coupling to actuate a first plunger to expel the first fluid from the first fluid reservoir and a second plunger to expel the second fluid from the second fluid reservoir.

8. The method of claim 1, further comprising expelling a coolant fluid from a coolant fluid reservoir and through a proximal portion of the probe after delivering thermal energy to the tissue to be treated.

9. A method for ablating tissue, the method comprising:
positioning an ablation device adjacent tissue to be treated, the ablation device including:
- a controller unit; and
- a probe operably coupled to the controller unit and including a heat-transfer portion in fluid communication with at least one of a first fluid-flow path or a second fluid-flow path, the first fluid-flow path in communication with a first fluid reservoir, the second fluid-flow path in communication with a second fluid reservoir, and the heat-transfer portion in fluid communication with a third fluid reservoir;

depressing a user-operable switch electrically coupled to the controller unit to expel a first fluid from the first fluid reservoir to contact a second fluid in the heat-transfer portion, thereby generating an exothermic chemical reaction; and delivering thermal energy released by the exothermic chemical reaction to the tissue to be treated.

10. The method of claim 9, wherein depressing the user-operable switch generates an electric signal from the controller unit to control an operation of at least one actuator.

11. The method of claim 9, further comprising expelling a coolant fluid from a coolant fluid reservoir and through a proximal portion of the probe after delivering thermal energy to the tissue to be treated.

12. The method of claim 9, further comprising energizing the controller unit with a self-contained power source.

13. The method of claim 12, further comprising providing a signal indication of a condition of the self-contained power source to a user.

14. The method of claim 9, further comprising monitoring a fluid flow of the first fluid expelled from the first fluid reservoir to the heat-transfer portion using a fluid-flow monitoring system.

15. The method of claim 14, further comprising regulating the fluid flow using the fluid-flow monitoring system.

16. The method of claim 15, further comprising monitoring a temperature of the heat-transfer portion using a temperature sensor in communication with the controller unit.

17. The method of claim 16, further comprising maintaining the temperature of the heat-transfer portion within a desired temperature range using the fluid-flow monitoring system.

18. The method of claim 17, wherein maintaining the temperature of the heat-transfer portion includes decreasing the fluid flow when the temperature of the heat-transfer portion is below the desired temperature range and increasing the fluid flow when the heat-transfer portion is above the desired temperature range.

* * * * *